United States Patent [19]
Burton et al.

[11] Patent Number: 4,895,991
[45] Date of Patent: Jan. 23, 1990

[54] METHOD OF PREPARATION OF TRIFLUOROMETHYL COPPER AND TRIFLUOROMETHYL AROMATICS

[75] Inventors: Donald J. Burton, Iowa City; Denise M. Wiemers, West Branch; Jerome C. Easdon, Iowa City, all of Iowa

[73] Assignee: University of Iowa Research Foundation, Iowa City, Iowa

[21] Appl. No.: 302,587

[22] Filed: Jan. 25, 1989

Related U.S. Application Data

[60] Continuation of Ser. No. 4,035, Jan. 16, 1987, abandoned, which is a continuation-in-part of Ser. No. 809,291, Dec. 16, 1985, Pat. No. 4,650,887, which is a division of Ser. No. 651,163, Sep. 17, 1984, Pat. No. 4,582,921.

[51] Int. Cl.[4] .................. C07C 17/26; C07C 17/28; C07C 17/24
[52] U.S. Cl. .................................. 570/144; 570/127
[58] Field of Search .......................... 570/144

[56] References Cited

U.S. PATENT DOCUMENTS

| | | | |
|---|---|---|---|
| 3,187,058 | 6/1965 | Patrick et al. | 570/144 |
| 3,280,202 | 10/1966 | Gilch | 570/144 |
| 3,408,411 | 10/1968 | McLaughlin et al. | 570/144 |
| 3,637,868 | 1/1972 | Nychka | 570/144 |

Primary Examiner—J. E. Evans
Attorney, Agent, or Firm—Zarley McKee, Thomte, Voorhees & Sease

[57] ABSTRACT

The process of direct synthesis of trifluoromethyl copper and trifluoromethyl aromatics, both intermediate reagents useful in direct synthesis of certain perfluoroalkyl compounds. The process involves a direct reaction between on the one hand an aromatic halide and a difluorodihalomethane and on the other hand copper and a difluorodihalomethane.

4 Claims, No Drawings

METHOD OF PREPARATION OF TRIFLUOROMETHYL COPPER AND TRIFLUOROMETHYL AROMATICS

This application is a continuation of Ser. No. 004,035, filed Jan. 16, 1987, now abandoned; which was a continuation-in-part of Ser. No. 809,291 filed Dec. 16, 1985, now U.S. Pat. No. 4,650,887 which issued Mar. 23, 1987; which itself was a division of Ser. No. 651,163 filed Sep. 17, 1984, now U.S. Pat. No. 4,582,921, which issued Apr. 15, 1986.

BACKGROUND OF THE INVENTION

Many organic compounds containing the trifluoromethyl group are extremely valuable compounds, useful in a variety of ways. For example, many agricultural chemicals which are herbicides, pesticides, and fungicides, contain the trifluoromethyl group attached to an aromatic ring. Perhaps one of the more famous is a herbicide sold under the trademark TREFLAN®. In addition, some well-known solvents have the trifluoromethyl moiety, as well as certain valuable chemical intermediates. In sum, there is a very real and continuing need for cheap, inexpensive and economic ways of introducing the trifluoromethyl group into both pharmaceutically active and agricultural chemically active compounds.

In the past, the synthetic routes for such compounds have been laborious. In particular, fluorinating agents used to prepare trifluoromethyl containing compounds have all been a compound which in fact already contained the trifluoromethyl group such as trifluoromethyl iodide, and bis(trifluoromethyl)mercury. These compounds are expensive, and not readily commercially available.

Contrasted with the expensive and difficult methods to obtain trifluoromethyl compounds, there are many cheap, commercially available difluorodihalomethanes, such as $CF_2Cl_2$, $CF_2BrCl$, and $CF_2Br_2$. However, no one has heretofore ever been able to achieve a direct synthesis of a trifluoromethyl organo metallic from a difluorodihalo methane compound.

Accordingly, it is a primary objective of the present invention to prepare trifluoromethyl organometallics from commercially available difluorodihalomethanes, such as dichlorodifluoromethane, chlorobromodifluoromethane, and dibromodifluoromethane.

Yet another objective of the present invention is to prepare trifluoromethyl organocadmium and zinc compounds from difluorodihalomethanes in a direct single step synthesis.

An even further objective of the present invention is to prepare stable trifluoromethyl copper reagents which are useful in further synthetic reactions to allow introduction of trifluoromethyl groups to other compounds.

A further objective of the invention is to prepare trifluoromethyl organometallic compounds of cadmium and zinc and copper which can be conveniently used to introduce the trifluoromethyl moiety to an olefinic derivative.

A further objective of the present invention is to prepare trifluoromethyl organometallic compounds of cadmium and zinc and copper which can be conveniently used to introduce the trifluoromethyl moiety into an aromatic compound.

A further objective of the present invention is to prepare trifluoromethyl organometallic compounds of cadmium and zinc and copper which can be conveniently used to introduce the trifluoromethyl moiety to an unsaturated organic compound, such as an acetylenic or an allylic compound.

A further objective of the present invention is to prepare trifluoromethyl organometallic compounds of cadmium and zinc and copper which can be conveniently used to introduce the trifluoromethyl moiety to an acyl derivative.

A further objective of the present invention is to prepare trifluoromethyl organometallic compounds of cadmium and zinc and copper which can be conveniently used to introduce the trifluoromethyl moiety for the preparation of other trifluoromethyl organometallics via metathesis reactions.

A still further objective is to prepare either directly or indirectly, perfluoroalkyl organometallic compounds of copper and other transition metals which can then be conveniently used to introduce a perfluoroalkyl group into an organic compound.

The method and manner of accomplishing each of the above objectives will become apparent from the detailed description of the invention which will follow hereinafter.

SUMMARY OF THE INVENTION

A process of preparing trifluoromethyl aromatics of the formula $Ar(CF_2)_nCF_3$ from a difluorodihalomethane of the formula $CF_2XY$ is described. The process involves a direct reaction between the aromatic halide and a difluorodihalomethane with copper to provide a trifluoromethyl aromatic. In another embodiment the reaction involves reacting copper and a difluorodihalomethane to provide a perfluoroalkyl copper reagent. These compounds are useful in a wide variety of synthetic reactions to introduce the trifluoromethyl moiety to the desired positions upon aromatics, such as aromatic halides, olefins, particularly halo olefins and acetylenic and allylic unsaturated compounds, and acyl derivatives as well. In a preferred process, the reaction is conducted in the presence of dimethylformamide.

DETAILED DESCRIPTION OF THE INVENTION

In accordance with the broadest aspect of this invention which involves preparing trifluoromethyl organo cadmium and zinc compounds, a compound of the formula $CF_2XY$, wherein X and Y are halogens, is reacted preferably with a metal selected from the group consisting of cadmium and zinc to provide a trifluoromethyl metal halide. X and Y may be the same or different, and are selected from the group of chlorine, bromine and iodine. Suitable compounds of this class include dichlorodifluoromethane, dibromodifluoromethane, and bromochlorodifluoromethane. The compound is reacted preferably with cadmium or zinc in order to provide stable compounds in a direct synthetic reaction represented by the following equation:

$$2\ CF_2XY \xrightarrow[\text{(DMF)}]{\text{Cd, Zn}} CF_3MX + (CF_3)_2M$$

X = Br, Cl, I
Y = Br, Cl, I

DMF=Dimethylformamide

The abbreviation "DMF" refers to dimethylformamide. It is currently not believed that dimethylformamide is critical, but the reaction must be conducted in the presence of an aprotic solvent since the cadmium reagent is hydrolyzed by water. Amongst those known to be suitable are dimethylformamide which is strongly preferred, methyl formamide, acetonitrile, and N-methylpyrolidine, and dimethylsulfide. The reaction is direct and will allow preparation in yields of 90–95% of the trifluoromethyl cadmium or zinc reagent. The reaction with the cadmium is faster than with zinc and at times is over in as little as a few minutes at room temperature. The reaction with the zinc compounds may take somewhat longer, and in the past has been run from time to time of from between eight and ten hours at 60° C.–70° C. Thus, in summary, the reaction will occur at temperatures ranging from about room temperature up to about 75° C., preferably for the zinc reaction from about 50° C. to about 75° C., and for the cadmium reaction may be at any temperature from room temperature up to about 75° C. The reaction time will run from a few minutes to a few hours. The trifluoromethyl cadmium or zinc reagent is stable and can be used for a variety of syntheses as described below.

The trifluoromethyl cadmium or zinc reagent prepared in accordance with this reaction can be used in an in situ preparation for introduction of the trifluoromethyl group into a variety of compounds.

In certain instances, because of its activity, it is also desirable to prepare trifluoromethyl copper reagents of the formula $CF_3Cu$. It is possible to prepare trifluoromethyl copper directly from the reaction of difluorodihalomethanes and copper; however, the $CF_3Cu$ undergoes chain elongation to form longer chain perfluoroalkyl copper reagents, unless the trifluoromethyl copper is trapped in situ. However, the cadmium and zinc reagents can be converted to a stable $CF_3Cu$, which itself is useful for trifluoromethylation. The trifluoromethyl cadmium or zinc reagent is reacted with a copper salt of the formula CuZ, wherein Z represents any solvent soluble anion which may be selected from, for example, the group of nitrate, phosphate, halides, including bromide, chloride and iodide, sulfate, acetate, trifluoroacetate, cyanide and the like. It is not critical what the anion is, only that it be solvent soluble for ease of introduction of the organo-copper into the reaction system. Again, the reaction should be conducted in the presence of an aprotic solvent and in fact may be conducted in situ in the same reaction vessel as the earlier preparation of the trifluoromethyl cadmium or zinc reagent.

Since the copper trifluoromethyl reagent can have stability problems in its preparation, it is desirable to run this reaction at temperatures of less than 0° C. A flask cooled with dry ice— isopropyl alcohol has been found to be satisfactory, with temperatures ranging from about 0° C. to −70° C. Ideally, temperatures within the range of −40° C. to −70° C. have been found satisfactory.

The preparation of trifluoromethyl aromatics is illustrated in Example 12 below. The preparation of perfluoroalkyl copper reagent is demonstrated in Example 13 below. In the formula: $Ar(CF_2)_nCF_3$, n represents the number of difluoromethyl groups and may be from 0–20, but preferably it is from 6–8. Likewise, as illustrated in Example 13 the formula: $CF_3(CF_2)_nCu$, n represents the same numbers, that is generally from 0–20, but preferably from about 6 to about 8.

Examples 17 and 18, shown below, also illustrate the preparation of copper perfluoroalkyl reagents (Example 17) and preparation of trifluoromethyl aromatics (Example 17 and in particular preparation of trifluoromethyl benzene, Example 18).

Other trifluoromethyl or perfluoroalkyl organometallics such as the trifluoromethyl tin reagent can be prepared via an analogous reaction of the difluorodihalomethanes directly the metal. In addition, other trifluoromethyl organometallics such as palladium, rhodium, platinum, gold cobalt, mercury or silver can be prepared by the indirect metathesis reaction of the appropriate metal salt with the trifluoromethyl cadmium reagent.

As heretofore stated, tifluoromethyl compounds have been generally prepared by substitution of fluorine for halogens such as bromine, chlorine, and iodine. Now, for the first time, they are available from a direct synthetic route from cheap and available difluorodihalomethanes.

The prepared trifluoromethyl reagent may be reacted in situ in many reactions in order to introduce the trifluoromethyl group into an aromatic ring, into an olefin at the point of unsaturation, or into an acetylenically or allylically unsaturated compound, or into an acyl derivative. The number of reactions which can be performed are almost limitless, but generally lower aromatics, lower $C_2$ to $C_{12}$ olefins, particularly halo olefins, and lower $C_2$ to $C_{12}$ acetylenically or allylically unsaturated compounds, and acyl derivatives can be conveniently used. All are illustrated in the examples. The following examples are offered to further illustrate, but not necessarily limit the process and products of this invention.

EXAMPLE 1

PREPARATION OF TRIFLUOROMETHYL CADMIUM FROM DIBROMODIFLUOROMETHANE

A three-neck 250 ml round bottom flask equipped with stopper, septum, magnetic stirbar and nitrogen tee was charged with 50 ml DMF and 22.4g(0.2 moles) activated cadmium. The $CF_2Br_2$ (9.1 ml, 0.1 moles) was added via a pre-cooled syringe. An exothermic reaction occurred and the solution turned dark brown. The reaction mixture was stirred for two hours at room temperature, then filtered through a medium-fritted schlenk funnel under nitrogen. The precipitate ($CdBr_2$) was washed with 10–15 ml DMF. The resulting filtrate was utilized in subsequent reactions. Typical yields of $CF_3CdX$ were 90–95% based on 2 moles of the methane being converted to 1 mole of cadmium reagent.

EXAMPLE 2

PREPARATION OF TRIFLUOROMETHYL CADMIUM FROM BROMOCHLORODIFLUOROMETHANE

The $CF_2BrCl$ was measured into a 15 ml graduated tube via a dry ice/IPA condenser (8.6 ml, 0.10 moles). Phosphorous pentoxide was added to the methane. The CF2BrCl was transferred to a similarly equipped flask as above except a dry ice/IPA condenser was added. The resulting exothermic reaction yields a dark brown solution which was filtered and washed as before. Typical yields were 90–95%.

EXAMPLE 3

PREPARATION OF TRIFLUOROMETHYL CADMIUM FROM DICHLORODIFLUOROMETHANE

A 300 ml sealed tube was charged with Cd(22.4g, 0.20 mole), $CF_2CL_2$ (8.1 ml, 0.10 mole) and 50 ml DMF. The reaction tube was heated to 80° C. for 24 hours. The resulting reaction mixture was pressure filtered through a medium fritted schlenk funnel and the precipitate was washed with 10-15 ml DMF.

EXAMPLE 4

PREPARATION OF TRIFLUOROMETHYL COPPER FROM THE TRIFLUOROMETHYL CADMIUM SOLUTION PREPARED FROM $CF_2BrCl$

The reaction mixture containing $CF_3CdX$ prepared previously was cooled to $-70°$ C. with a dry ice/IPA bath. Cuprous bromide (7.2g, .05 moles) was added to the cooled flask and warmed slightly ($-50°$ C.) for efficient stirring. The reaction mixture was used at this temperature in subsequent reactions. At higher temperatures the $CF_3Cu$ decomposes. Typical yields for $CF_3Cu$ (based on $CF_3Cd$) are 90-95%.

EXAMPLE 5

UTILIZATION OF THE TRIFLUOROMETHYL COPPER SOLUTION WITH ALLYLIC HALIDES

Typical procedures

The $CF_3Cu$ solution was cooled to $-70°$ C. and the allyl halide (0.03 moles) was added. The solution was slowly warmed to room temperature. The solution was stirred at room temperature for 2-4 hours, steam distillation followed by fractional distillation resulted in isolated yields of 50-75%.

EXAMPLE 6

FORMATION OF $CF_3X$; X=I, D

Typical procedure

The solution containing $CF_3CdBr$ is cooled to 0° C. with an ice bath and $I_2$ or $D_2O$ is slowly added. Flash distillation followed by trap to trap distillation resulted in $CF_3I$ (24%) and $CF_3D$ (34%).

EXAMPLE 7

FORMATION OF $CF_3Ar$

The solution containing the cadmium reagent was utilized. An equal volume of HMPA (Hexamethylphosphoramide) was added to the cadmium reagent solution. Cuprous bromide (7.2g, 0.05 moles) was added at room temperature. The aromatic compound (0.020 moles) was added to the solution and was heated to 60-70° C. for four hours. The reaction mixture was steam distilled, the organic layer separated and fractionally distilled. Typical yields (based on aromatic halide) were 60-80%.

EXAMPLE 8

FORMATION OF TRIFLUOROMETHYLATED OLEFINS

Typical procedure

The solution containing the copper reagent at $-70°$ C. was utilized in the formation of trifluoromethylated olefins. The vinyl halide was added to the copper reagent at $-70°$ and slowly allowed to warm to room temperature. The reaction mixture was flash distilled. The flash distillate was washed with water and the organic layer separated. The olefin was fractionally distilled. Typical yields (based on vinyl halide) were 40-69%.

EXAMPLE 9

PREPARATION OF PERFLUOROETHYL COPPER FROM TRIFLUOROMETHYLCOPPER

The copper reagent prepared at $-70°$ C. was slowly allowed to warm to room temperature. Perfluoroethyl copper was obtained in 90% yield based on trifluoromethyl copper. A solution of $I_2$ in DMF was added to the ethyl copper reagent. The reaction mixture was flash distilled followed by trap to trap distillation resulted in a 65% isolated yield of perfluoroethyl iodide.

EXAMPLE 10

PREPARATION OF TRIFLUOROMETHYL ZINC FROM BROMOCHLORODIFLUOROMETHANE

A three-necked 100 ml round bottomed flask, equipped with a dry ice/IPA condenser, magnetic stirbar, septum and stopper was charged with 50 ml of DMF and activated zinc (6.3g, 0.10 moles). The methane (8.6 ml, 0.05 moles) was added via the dry ice/IPA condenser and the solution was heated for 8-10 hours at 65-70° C. The resulting solution was filtered through a medium-fritted schlenk funnel. The yield of the trifluoromethyl zinc was 50-60% based on starting methane.

EXAMPLE 11

FORMATION OF TRIFLUOROMETHYL KETONES FROM THE TRIFLUOROMETHYL ZINC

The trifluoromethyl zinc reagent was cooled to $-20-(-30°$ C.) and the acid chloride was added. The reaction mixture was warmed to room temperature and allowed to stir overnight. Flash distillation followed by addition of water and separation of the organic layer gave a yield (40%) of the trifluoromethylated ketone.

EXAMPLE 12

PREPARATION OF TRIFLUOROMETHYL AROMATICS

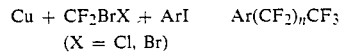

$$Cu + CF_2BrX + ArI \longrightarrow Ar(CF_2)_nCF_3$$
$$(X = Cl, Br)$$

| Materials: | |
|---|---|
| Cu | 1.91 g. (30 mmoles) |
| $CF_2BrX$ | 0.91 ml (X=Br, 0.86 ml (X=Cl) (10 mmoles) |
| ArI | 5 mmoles |
| Dimethylformamide (DMF) | 10 ml. |

Procedure

The copper metal was weighed into a 25 ml. round bottom flask which was equipped with a septum. A dry ice/acetone condenser was placed on the flask and the apparatus was maintained under nitrogen atmosphere. DMF, aromatic iodide and $CF_2BrX$ were added to the flask. The reaction mixture was stirred and heated with an oil bath until it appeared that all of the copper metal has been converted to copper halide.

Yields ($^{19}$F-NMR) are usually greater than 60%, based upon the amount of aromatic iodide converted to perfluoroalkyl aromatics. A mixture of perfluoroalkyl aromatics was generally obtained, although the trifluoromethylated aromatic is the major product. The highest proportion of the trifluoromethyl product was obtained utilizing $CF_2BrCl$ at a temperature of 85° C.

The chain extension can be suppressed by the addition of any fluoride ion (CsF, KF) and other soluble fluoride salts such as Groups I and II metals. It may also be possible to use any other fluoride ion source. This gave mixtures with much larger proportions of the trifluoromethylated aromatic compound. Less copper metal was consumed, although the reaction time was longer.

EXAMPLE 13

PREPARATION OF PERFLUOROALKYL COPPER REAGENTS

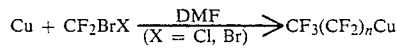

| Materials: | |
|---|---|
| Cu | 1.91 g. (30 mmoles) |
| $CF_2BrX$ | 0.91 ml (X=Br), 0.86 ml (X=Cl), (10 mmole) |
| Dimethylformamide (DMF) | 10 ml. |

Procedure

The finely divided copper metal was weighed into a 25 ml round bottom flask which was equipped with a septum. A dry ice/acetone condenser was placed on the flask and the apparatus was equipped with an oil bubbler and maintained under a nitrogen atmosphere. DMF and $CF_2BrX$ were added to the flask. The reaction mixture was stirred and heated with an oil bath until it appeared that all of the copper metal has been converted to copper halide.

Typical yields ($^{19}$F-NMR) are around 60%. The products obtained were a mixture of perfluoroalkyl copper reagents. The chain lengths ranged from 2 to 17 carbons (detected by GC/MS), but the major products were F-ethyl, F-propyl and F-butyl copper. The product distribution was a function of temperature and X. The best proportions of F-ethyl copper (~80%) was obtained using $CF_2BrCl$ and 70° C. Using $CF_2Br_2$ at 80° C. gives the product distribution with the highest proportion of F-butyl copper and higher homologous copper reagents (~80%).

EXAMPLE 14

PREPARATION OF PERFLUOROETHYL AROMATIC COMPOUNDS

The perfluoroethyl copper was prepared as previously described. An aromatic iodide was added to this solution and heated to 60° -70° C. for four to six hours. After the reaction was complete, the reaction mixture was steam distilled. The organic and aqueous layers were separated and the aqueous layer extracted with (3×20 ml) pentane. The pentane layer was dried over anhydrous $MgSO_4$. The pentane was either distilled or removed under reduced pressure depending on the property of the product.

EXAMPLE 15

PREPARATION OF TRIFLUOROMETHYL TIN HALIDE

A three-neck 50 ml round bottom flask equipped with stopper, septum, magnetic stirbar and nitrogen tee was charged with 20 ml DMF and 11.9 g (0.1 mole) Sn. The $CF_2Br_2$ (4.6 ml, 0.05 mole) was added via precooled syringe. An exothermic reaction occurred and the reaction mixture turned dark brown. Subsequent analysis confirmed the presence of $(CF_3)_n Sn\ X$, wherein n=1-4 or in other words, $(CF_3)SnX_3$, $(CF_3)_2SnX_2$, $(CF_3)_3SnX$, $(CF_3)_4Sn$.

EXAMPLE 16

PREPARATION OF VARIOUS ORGANOMETALLICS FROM $CF_3CdX$

A solution of $CF_3CdX$ in DMF was reacted with each of the following metal halide complexes to yield the corresponding trifluoromethyl organometallic derivative.

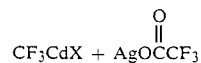

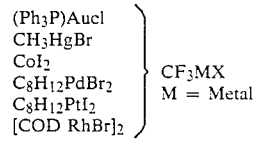

EXAMPLE 17

PREPARATION OF $CF_3(CF_2)_nCu$ AND $CF_3(CF_2)_nAr$

Copper (1.91 g, 0.030 moles) was added to a 25 ml round bottom flask fitted with a rubber septum and magnetic stir bar. The flask was attached to a Dry/Ice isopropyl alcohol condenser. DMF (10 ml) was added to the flask followed by the addition of $CF_2BrCl$ (1 ml, 0.010 moles). The reaction mixture was heated to 65 to 105° C. until the $CF_2BrCl$ was consumed. $^{19}$F NMR analysis indicated the presence of $CF_3(CF_2)_nCu$, where n=1,2,3 etc...

The cooled reaction mixture was filtered through a medium frit Schlenk funnel into a dry round bottom flask equipped with a magnetic stir bar and water condenser. Iodobenzene (equivalent to the amount of perfluoroalkyl copper reagents calculated by 19F NMR as indicated above) was added and the reaction mixture was then heated to 100° C. for two hours. Steam distillation of the reaction mixture yielded perfluoroalkyl benzenes as a lower organic layer. The relative ratios of these perfluoroalkyl benzenes were determined by GC/MS and a series of $CF_3(CF_2)_nC_6H_5$ (where n=0-14) were found. The value of n and the amount of each perfluoroalkyl benzene derivative depended on the temperature and the $CF_2XY$ precursor utilized.

EXAMPLE 18

PREPARATION OF TRIFLUOROMETHYL BENZENE

A 300 ml Hastelloy C Parr bomb was charged with 25.42 g (0.40 mole) of copper-bronze; DMF (200 mls), iodobenzene (20.62 g, 0.10 mole); 33.1 g (0.20 mole) $CF_2BrCl$; and 11.62 g (0.10 mole) of potassium fluoride (KF). The sealed bomb was heated at 95° C for 88 hours, cooled to room temperature, the pressure released, and the contents of the bomb transferred to a 500 ml round bottom flask and steam distilled to give 16.88 g of an organic layer. GLPC analysis showed no iodobenzene. GLPC analysis indicated a ratio of trifluoromethyl benzene to other perfluoroalkyl benzenes of 90:10. The organic product was further purified by spinning band distillation to give 7.78 g (0.053 mole) of 97.9% pure (by GLPC) trifluoromethyl benzene for a 53% yield. $^1H$ NMR exhibits a multiplet at 7.5 ppm ($CDCl_3$, TMS), and the $^{19}F$ NMR exhibits a singlet at $-63.2$ ppm ($CDCl_3$, $CFCl_3$). IR Spectrum: 3060 cm$^{-1}$ (w), 1320 cm$^{-1}$ (s), 1125 cm$^{-1}$ (s), 1068 cm$^{-1}$ (m), 1025 cm$^{-1}$ (w), 765 cm$^{-1}$ (w).

As illustrated in the examples, and in particular in Examples 12 and 18, potassium fluoride addition suppresses chain growth, leaving the formation of the trifluoromethyl aromatics as opposed to the formation of perfluoroalkyl copper reagent such as in Example 13. The chain suppression by the addition of the fluoride ion can be accomplished with any soluble fluoride, but it is particularly preferred that it be selected from cesium fluoride and potassium fluoride. The amount of fluoride used is preferably an equimolar amount with the aromatic iodide, but may vary from about 0.5 moles per mole of aromatic iodide to about 1.5 times the molar amount of aromatic iodide. It is preferably equimolar. As seen in Example 17, where there is no chain suppression, the product formed may be a mixture of perfluoroalkyl aromatics and trifluoromethylated aromatic.

It thus can be seen that the invention accomplishes as least all of its stated objectives.

What is claimed is:

1. The method of preparation of trifluoromethyl aromatics of the formula $Ar(CF_2)_nCF_3$ from a difluorodihalomethane of the formula $CF_2XY$, comprising:

reacting an aromatic halide with a difluorodihalomethane of the formula $CF_2XY$ wherein X and Y are halogens but are not fluorine, with copper metal in the presence of a small but chain extension suppression effective amount of fluoride ion to provide a perfluoroalkyl aromatic of the formula $Ar(CF_2)_nCF_3$, wherein n is from 0 to 20.

2. The method of claim 1 wherein n is from about 6 to about 8.

3. The method of claim 1 wherein said fluoride ion is a Group I fluoride.

4. The method of claim 3 wherein said fluoride ion is selected from the group consisting of cesium fluoride and potassium fluoride.

* * * * *